United States Patent
Chen et al.

(10) Patent No.: US 10,577,334 B2
(45) Date of Patent: Mar. 3, 2020

(54) CRYSTALLINE FORM E OF TAFAMIDIS MEGLUMINE, PROCESS FOR PREPARATION AND USE THEREOF

(71) Applicant: Crystal Pharmatech Co., Ltd., Suzhou, Jiangsu (CN)

(72) Inventors: Minhua Chen, Suzhou (CN); Yanfeng Zhang, Suzhou (CN); Jiaoyang Li, Suzhou (CN); Xiaoyu Zhang, Suzhou (CN)

(73) Assignee: Crystal Pharmatech Co., Ltd., Suzhou (CN)

( * ) Notice: Subject to any disclaimer, the term of this patent is extended or adjusted under 35 U.S.C. 154(b) by 0 days.

(21) Appl. No.: 16/098,586

(22) PCT Filed: May 5, 2017

(86) PCT No.: PCT/CN2017/083177
§ 371 (c)(1),
(2) Date: Nov. 2, 2018

(87) PCT Pub. No.: WO2017/190682
PCT Pub. Date: Nov. 9, 2017

(65) Prior Publication Data
US 2019/0119226 A1    Apr. 25, 2019

(30) Foreign Application Priority Data

May 5, 2016 (CN) .......................... 2016 1 0293338

(51) Int. Cl.
| | | |
|---|---|---|
| *C07D 263/57* | (2006.01) | |
| *C07C 215/40* | (2006.01) | |
| *A61K 31/423* | (2006.01) | |
| *A61P 25/28* | (2006.01) | |

(52) U.S. Cl.
CPC .......... *C07D 263/57* (2013.01); *A61K 31/423* (2013.01); *A61P 25/28* (2018.01); *C07C 215/40* (2013.01); *C07B 2200/13* (2013.01)

(58) Field of Classification Search
CPC .. A61K 31/423; C07C 215/40; C07D 263/57; A61P 25/28; C07B 2200/13
See application file for complete search history.

(56) References Cited

FOREIGN PATENT DOCUMENTS

| CN | 103781770 A | 5/2014 | |
|---|---|---|---|
| JP | 2014-526498 A | 10/2014 | |
| WO | WO-2013038351 A1 * | 3/2013 | ........... C07D 263/57 |

OTHER PUBLICATIONS

Plante-Bordeneuve et. al., J. Neurology, 2014, Springer, vol. 261, pp. 1227-1233 (Year: 2014).*
Coelho et al., Tafamidis for transthyretin familial amyloid polyneuropathy: a randomized, controlled trial. Neurology. Aug. 21, 2012;79(8):785-92.
Nencetti et al., Tafamidis (Vyndaqel): a light for FAP patients. ChemMedChem. Oct. 2013;8(10):1617-9.
Guideline for residual solvents in pharmaceuticals. Medicine. Mar. 30, 1998;307:13 pages.
Hirayama, Organic Compound Crystal Production Manual: Principle and Know-How. Maruzen Co., Ltd. Jul. 25, 2008;17-23, 37-40, 45-51 and 57-65.
Oshima et al., Crystallization of Polymorphs and Pseudo-polymorphs and Its Controls. Pharm Stage. Jan. 2007;6 (10):48-53.

* cited by examiner

*Primary Examiner* — Sarah Pihonak
(74) *Attorney, Agent, or Firm* — McCarter & English, LLP; Steven G. Davis; Wei Song

(57) ABSTRACT

The present disclosure relates to a novel crystalline form E of Tafamidis meglumine, process for preparation and use thereof. When compared with prior crystalline forms, the novel crystalline form of the present disclosure has the advantages of simple process and low hygroscopicity, which provides a new and better choice for the development of Tafamidis meglumine drug product and is of great significance.

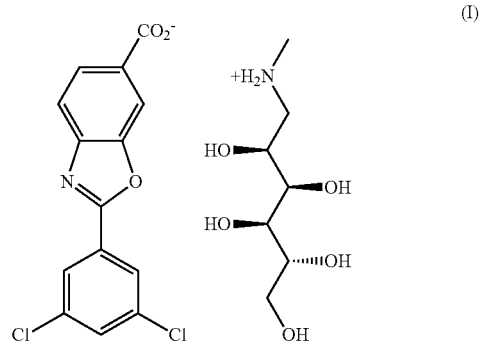

9 Claims, 5 Drawing Sheets

CRYSTALLINE FORM E OF TAFAMIDIS MEGLUMINE, PROCESS FOR PREPARATION AND USE THEREOF

CROSS-REFERENCE TO RELATED APPLICATIONS

The present application is a U.S. national stage application, filed under 35 U.S.C. § 371(c), of International Application No. PCT/CN2017/083177, filed on May 5, 2017, which claims the priority of Chinese Application No. 201610293338.X, filed on May 5, 2016. The entire contents of the aforementioned application are incorporated herein by reference.

TECHNICAL FIELD

The present disclosure relates to the technical field of pharmaceutical crystal. In particular, it relates to a novel crystalline form of Tafamidis meglumine, process for preparation and use thereof.

BACKGROUND

The present disclosure relates to a solid form of 6-carboxy-2-(3, 5-dichlorophenyl)-benzoxazole meglumine salt, also named as Tafamidis meglumine, which is used for treating transthyretin amyloidosis in mammal. Tafamidis meglumine stabilizes the protein transthyretin (TTR), dissociation of which is implicated in TTR amyloidosis and is being developed for the treatment of transthyretin familial amyloid polyneuropathy. Tafamidis meglumine is developed by Pfizer and is marketed in the European Union as Vyndaqel since 2011. The structure is shown as formula (I):

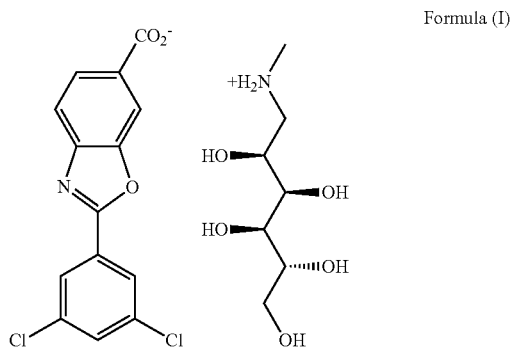

Formula (I)

Polymorph or polymorphism is the property of some molecules or molecular complexes. Polymorphism may result from different molecular packing. Polymorphs of a given compound may have different crystal structures and physical properties, such as solubility, stability, thermal property, mechanical property, purification ability, X-ray powder diffraction, infrared spectroscopy, Raman spectroscopy, and solid-state NMR spectroscopy, etc. One or combination of multiple characterization methods may be used to differentiate different crystalline forms of the same molecule or molecular complexes. Novel crystalline forms (including anhydrates, hydrates and solvates) of the active pharmaceutical ingredients may offer better processing and physicochemical properties, such as bioavailability, stability, processability, and purification ability. Some novel crystalline forms may serve as intermediate crystal forms to facilitate solid state transformation to desired forms. Novel polymorphs of raw materials provide more solid forms in the formulation, and this can improve dissolution, improve shelf life, and make it easier to process.

CN100448852C firstly disclosed the preparation and salts of Tafamidis. CN103781770B disclosed crystalline form M, liquid crystalline form B and amorphous form A of Tafamidis meglumine (which is incorporated herein by reference). The amorphous form A has poor stability and would convert to liquid crystalline form B spontaneously when stored for some time. Liquid crystalline form B is highly deliquescent and the weight gain is up to 25% when stored at 90% relative humidity, thus form B is not suitable for drug development. By now, crystalline form M is the only form which can be used for drug development, and is also used for scaled up production of active pharmaceutical ingredients (API). The X-ray powder diffraction pattern of crystalline form M shows diffraction peaks at 2 theta values of 10.7°±0.2°, 11.8°±0.2°, 13.3°±0.2°, 14.8°±0.2° and 21.7°±0.2°. In addition to the above-described polymorphs, no other crystalline form is disclosed. Studies show that hygroscopicity of crystalline form M is high, thus resulting in high cost in storage. Therefore, it is still significant to develop a novel crystalline form with lower hygroscopicity that can be used for drug development. With lots of experiments being carried out, inventors of the present application finally find novel crystalline form E of Tafamidis meglumine which is beneficial for production and development process. The crystalline form E has advantages of good stability, simple preparation process, low hygroscopicity and good purification effect. It is also beneficial to drug's long-term storage. Crystalline form E provides a new and better choice for the development of Tafamidis meglumine drug product.

SUMMARY

The main objective of the present disclosure is to provide a novel crystalline form of Tafamidis meglumine, process for preparation and use thereof, which is a better choice for drug development.

According to the objective of the present disclosure, crystalline form E of Tafamidis meglumine (hereinafter referred to as Form E) is provided. Compared with crystalline form M, Form E has low hygroscopicity, simple preparation process and good stability which is more suitable for drug development.

Using Cu—Kα radiation, the X-ray powder diffraction pattern of Form E shows diffraction peaks at 2 theta values of 8.9°±0.2°, 17.7°±0.2° and 19.5°±0.2°. Furthermore, the X-ray powder diffraction pattern of Form E shows 1 or 2 or 3 diffraction peaks at 2 theta values of 22.5°±0.2°, 23.8°±0.2° and 28.2°±0.2°.

Furthermore, the X-ray powder diffraction pattern of Form E shows 1 or 2 diffraction peaks at 2 theta values of 15.4°±0.2° and 22.9°±0.2°.

Preferably, the X-ray powder diffraction pattern of Form E shows diffraction peaks at 2 theta values of 8.9°±0.2°, 17.7°±0.2°, 19.5°±0.2°, 22.5°±0.2°, 23.8°±0.2°, 28.2°±0.2°, 15.4°±0.2° and 22.9°±0.2°.

Without any limitation being implied, in a specific embodiment of the present disclosure, the X-ray powder diffraction pattern of Form E is substantially as depicted in FIG. 1.

Without any limitation being implied, in a specific embodiment of the present disclosure, when performing differential scanning calorimetry (DSC), Form E of the present disclosure shows three endothermic peaks at the temperature of around 118° C. (onset temperature), 155° C. (onset temperature), and 187° C. (onset temperature). The DSC curve of Form E is substantially as depicted in FIG. 3.

Without any limitation being implied, in a specific embodiment of the present disclosure, when performing thermogravimetric analysis, Form E of the present disclosure shows about 2.6% weight loss when heated to 120° C. The TGA curve of Form E is substantially as depicted in FIG. 4.

According to the objective of the present disclosure, a process for preparing Form E is also provided. The process comprises: adding ketones, ethers or esters into a mixture of Tafamidis free acid and meglumine, stirring to crystallize at room temperature, and then separating and drying to obtain Form E.

Wherein:

Preferably, said ketone is methyl isobutyl ketone;

Preferably, said ether is methyl tert-butyl ether;

Preferably, said ester is ethyl acetate;

When Tafamidis free acid is used as starting material, the mole ratio of Tafamidis free acid and meglumine is 1:1 to 1.5:1, preferably 1:1.

Preferably, said reaction or operation is performed at the temperature of 25° C.;

Preferably, said crystallization time is 12 to 72 hours, more preferably 24 hours.

In the preparation process of Form E of the present disclosure:

Said "room temperature" is 15 to 30° C.

Said "stirring" is accomplished with the conventional methods in this field, such as magnetic stirring or mechanical stirring; the stirring speed is 50-1800 rpm, and preferably, 300-900 rpm.

Said "separating" is accomplished by conventional methods in this filed, such as centrifugation and filtering. The operation of "centrifugation" comprises placing the sample into a centrifuge tube, then spinning at 10000 rpm until all the solids sink to the bottom of the tube.

Unless otherwise specified, said "drying" may be conducted at room temperature or higher temperature. The drying temperature is from room temperature to 60° C., or to 40° C., or to 50° C. The drying time may be 2 to 48 hours, or overnight. Drying may be conducted in a fume hood, an air convection drying oven or a vacuum drying oven.

In the present disclosure, "crystal" or "crystalline form" refers to the crystal or the crystal form being identified by the X-ray diffraction pattern shown herein. The person skilled in the art are able to understand that physical and chemical properties discussed herein can be characterized and the experimental errors depend on the conditions of instruments, the sample preparations and the purity of samples. In particular, those skilled in the art generally know that the X-ray diffraction pattern usually may change with the change of the experimental conditions. It is necessary to point out that, the relative intensity of the X-ray diffraction pattern is likely to change with the change of the experimental conditions; therefore, the sequence of peak intensity cannot be regarded as the only or the determining factor. Moreover, the experimental error of the peak positions is 5% or less, so such error should be considered and generally the allowed error is ±0.2° 2θ. In addition, due to the effect of the experimental factors including sample height, positions may have an overall shifting; generally, certain shifting is allowed. Hence, those skilled in the art may understand that, it is unnecessary that the X-ray diffraction pattern of a crystal form in the present disclosure should be exactly the same with X-ray diffraction patterns of the example shown herein. Any crystal forms whose X-ray diffraction patterns have the same or similar characteristic peaks should be within the scope of the present disclosure. Those skilled in the art can compare the patterns shown in the present disclosure with that of an unknown crystal form in order to identify whether these two groups of patterns reflect the same or different crystal forms.

"Crystalline form" and "polymorphic form" as well as other related terms in the present disclosure refer to a specific crystal form of solid compounds. The difference in the physical and chemical properties of the polymorphic forms may include stability during storage, compressibility, density, dissolution rate, etc. In extreme cases, the difference in solubility or dissolution rate may result in drugs with low efficiency and toxicity.

The term "effective treatment amount" or "therapeutically effective amount" as used herein means that amount of an active compound that elicits the biological or medicinal response in a tissue, system, animal or human that is being sought by a researcher, veterinarian, medical doctor, or other clinician.

As used herein, the term "treatment" refers to one or more of the following: (1) Inhibiting the disease, for example, inhibiting the disease, illness or disorder in an individual who is suffering from or displaying a lesion or symptom of the disease, illness or disorder, and (2) Improving the disease, for example, improving the disease, illness or disorder in an individual who is suffering from or displaying a lesion or symptom of the disease, illness or disorder (that is to reverse the lesion and/or symptoms), for example, reducing the severity of the disease.

In some embodiments, Form E of the present disclosure is substantially free of any other crystalline forms. In the present disclosure, when the term "substantially free" is used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the numerical value and the scope of the present disclosure should not be narrowly understood as a value or numerical value range itself. It should be understood by those skilled in the art that the specific numerical value can be varied or modified in specific technical environment without departing substantially from the spirit and principles of the disclosure, and the range of variation which can be expected by one of skilled in the art is represented by the term "about".

In addition, the present disclosure provides a pharmaceutical composition. Said pharmaceutical composition comprises a therapeutically or prophylactically effective amount of Form E and at least one pharmaceutically acceptable carrier, diluent or excipient. Additionally, said pharmaceutical composition can also comprise other pharmaceutically acceptable crystalline or amorphous forms of Tafamidis meglumine. Said other pharmaceutically acceptable crystalline forms of Tafamidis meglumine include but is not limited to the known crystalline forms disclosed in prior art, such as the crystalline forms disclosed in CN103781770B.

In addition, the present disclosure provides the use of Form E of Tafamidis meglumine for preparing drugs treating diseases associated with transthyretin amyloidosis.

The present disclosure provides the use of Form E of Tafamidis meglumine for preparing drugs treating transthyretin familial amyloid polyneuropathy.

In addition, the present disclosure provides a method for treating or preventing transthyretin familial amyloid polyneuropathy. Said method comprises administering a therapeutically or prophylactically effective amount of Form E of Tafamidis meglumine, or pharmaceutical composition comprising Form E to patients in need. Said patients include but are not limited to mammal, and said mammal can be human being.

DETAILED DESCRIPTION OF THE DISCLOSURE

Figure 1:
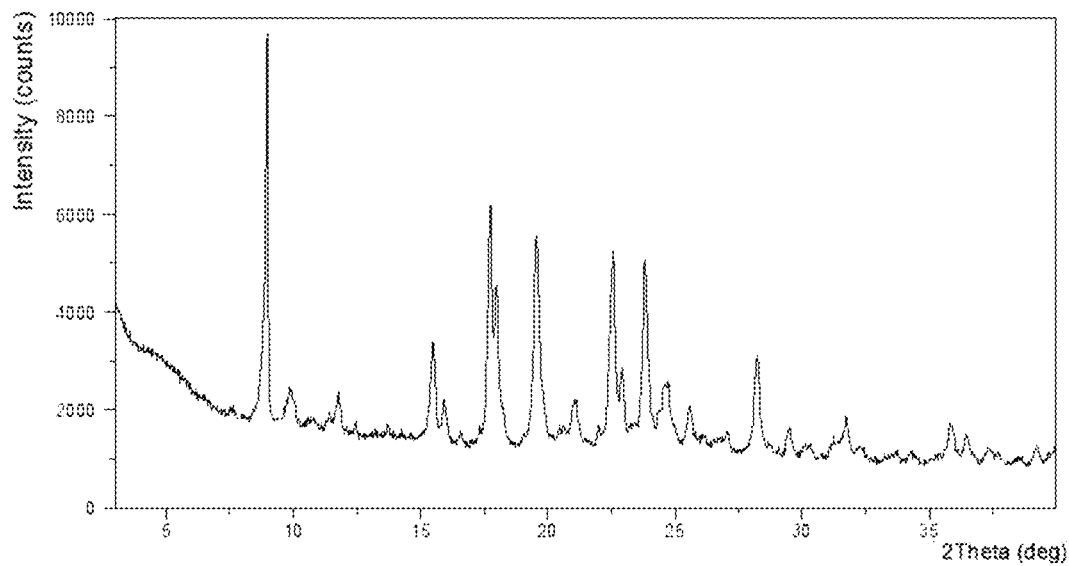
FIG. 1 shows an X-ray Powder Diffraction pattern of Form E in example 1.

The present disclosure is further illustrated by the following examples which describe the preparation and use of the crystalline form of the disclosure in detail. It is obvious to those skilled in the art that many changes in the materials and methods can be accomplished without departing from the scope of the disclosure.

The instruments and methods used to collect data:

X-ray powder diffraction (XRPD) pattern in the present disclosure is acquired by a Panalytical Empyrean X-ray powder diffractometer. The parameters of the X-ray powder diffraction method of the present disclosure are as follows:

X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree The data of differential scanning calorimetry (DSC) are acquired by a TA Instruments Q2000 MDSC, with Thermal Advantage as instrument control software and Universal Analysis as analysis software. Generally, 1~10 mg of sample is put into an aluminum crucible (unless otherwise specified, the aluminum crucible is covered). The temperature of sample was raised from room temperature to 300° C. with a heating rate of 10° C./min under the protection of dry nitrogen with a flow rate of 50 mL/min, while the TA software records the heat change of the sample during the heating process. In the present disclosure, melting point is reported based on DSC onset temperature.

The data of thermogravimetric analysis (TGA) are acquired by a TA Instruments Q5000 TGA, with Thermal Advantage as instrument control software and Universal Analysis as analysis software. Generally, 5~15 mg of sample is put into a platinum crucible. With segmented high resolution detection, the temperature of sample was raised from room temperature to 300° C. with a heating rate of 10° C./min under the protection of dry nitrogen with a flow rate of 50 mL/min, while the TA software records the weight change of the sample during the heating process.

Proton Nuclear Magnetic Resonance ($^1$HNMR) spectrum data are collected from a Bruker Avance II DMX 400M HZ NMR spectrometer. 1-5 mg of sample was weighed, dissolved in 0.5 mL of deuterated dimethyl sulfoxide to obtain a solution with the concentration of 2-10 mg/mL.

High Performance Liquid Chromatography (HPLC) data in the present disclosure are collected from Agilent 1260 with diode array detector (DAD). The HPLC method parameters for purity test in the present disclosure are as follows:

1. Column: Waters Xbridge C18 150×4.6 mm, 5 μm
2. Mobile Phase: A: 0.1% TFA in $H_2O$
B: 0.1% TFA in Acetonitrile
Gradient:

| Time (min) | % B |
| --- | --- |
| 0.0 | 10 |
| 3.0 | 10 |
| 20.0 | 90 |
| 25.0 | 90 |
| 25.1 | 10 |
| 30.0 | 10 |

3. Flow rate: 1.0 mL/min
4. Injection Volume: 5 μL
5. Detection wavelength: 280 nm
6. Column Temperature: 40° C.
7. Diluent: 1.2 mL of Acetonitrile and 100 μL of dimethyl sulfoxide Unless otherwise specified, the following examples were conducted at room temperature.

Tafamidis free acid used in the following examples can be purchased from market. Crystalline form M is prepared by the process in CN103781770B.

EXAMPLE 1

50.1 mg of Tafamidis free acid and 31.7 mg of meglumine were mixed evenly, and were added into 2.5 mL of ethyl acetate. The mixture was stirred at room temperature for 20 hours to crystallize. White crystalline solid of Tafamidis meglumine was obtained by centrifugation and vacuum drying at room temperature.

Figure 3:
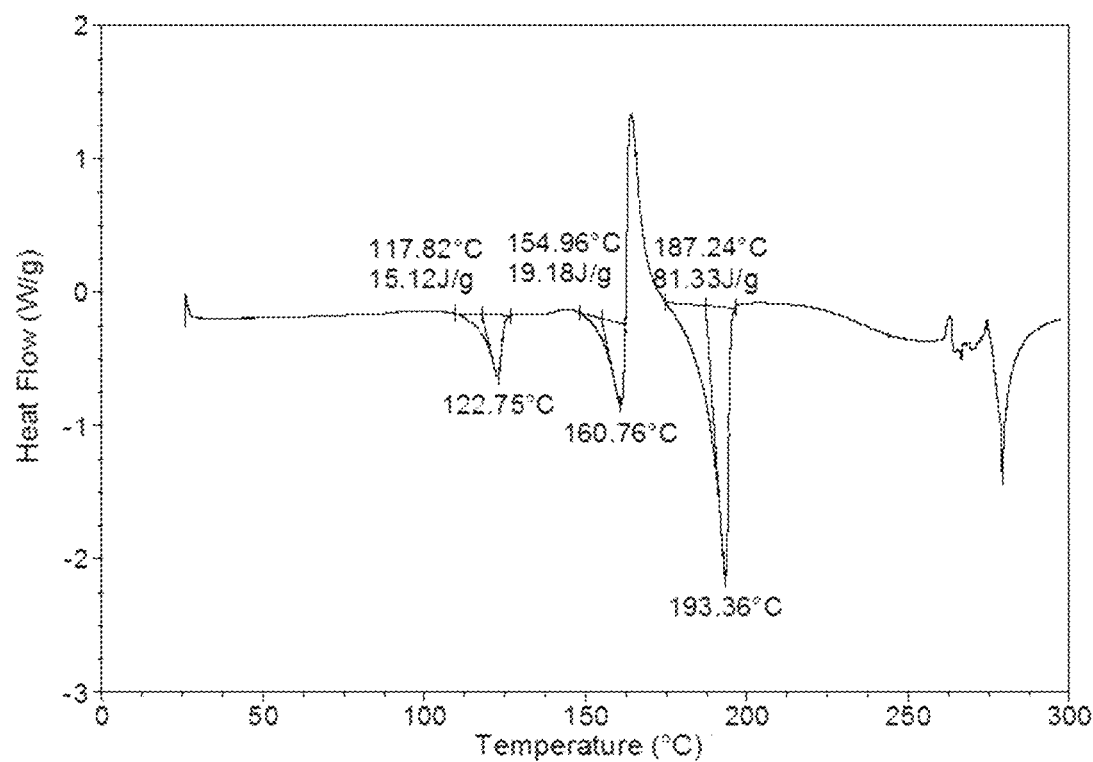
FIG. 3 shows a Differential Scanning calorimetry curve of Form E in example 1.

The obtained crystalline solid conformed to Form E of the present disclosure. Its XRPD pattern was substantially as depicted in FIG. 1, and the XRPD data were listed in Table 1. The DSC curve of Form E was substantially as depicted in FIG. 3, which comprises three endothermic peaks. Onset of the first endothermic peak is around 118° C., and the second is around 155° C. The third endothermic peak at 187° C. corresponds to the melting process.

Figure 4:
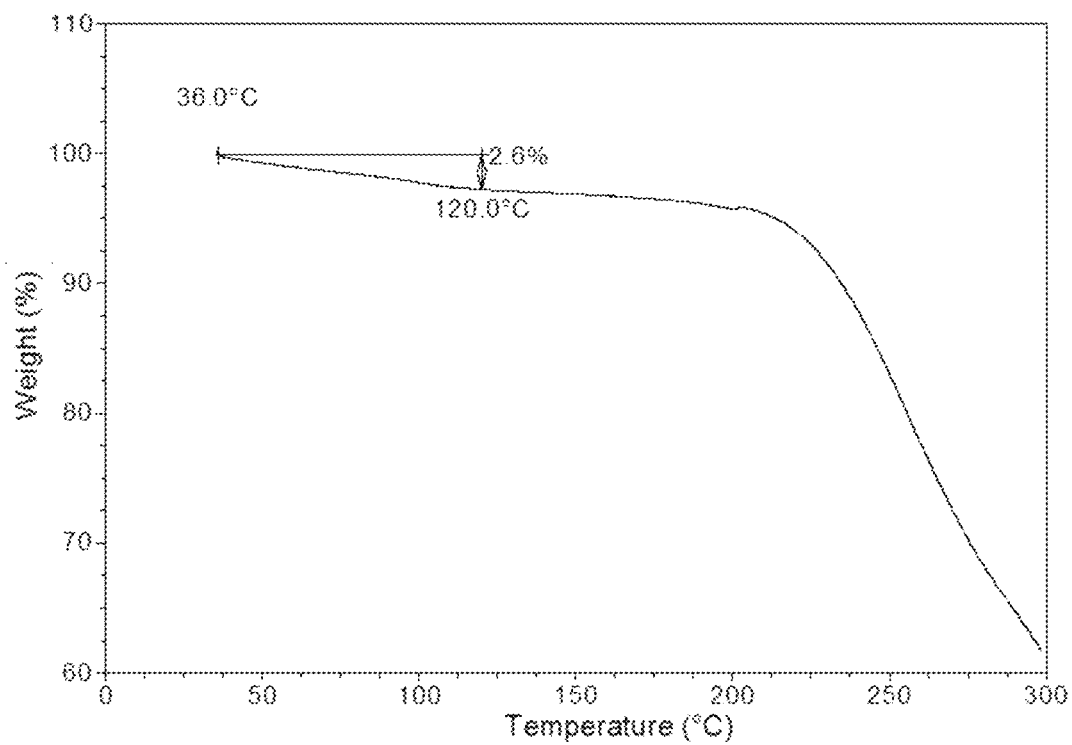
FIG. 4 shows a Thermal Gravimetric Analysis curve of Form E in example 1.
Figure 5:
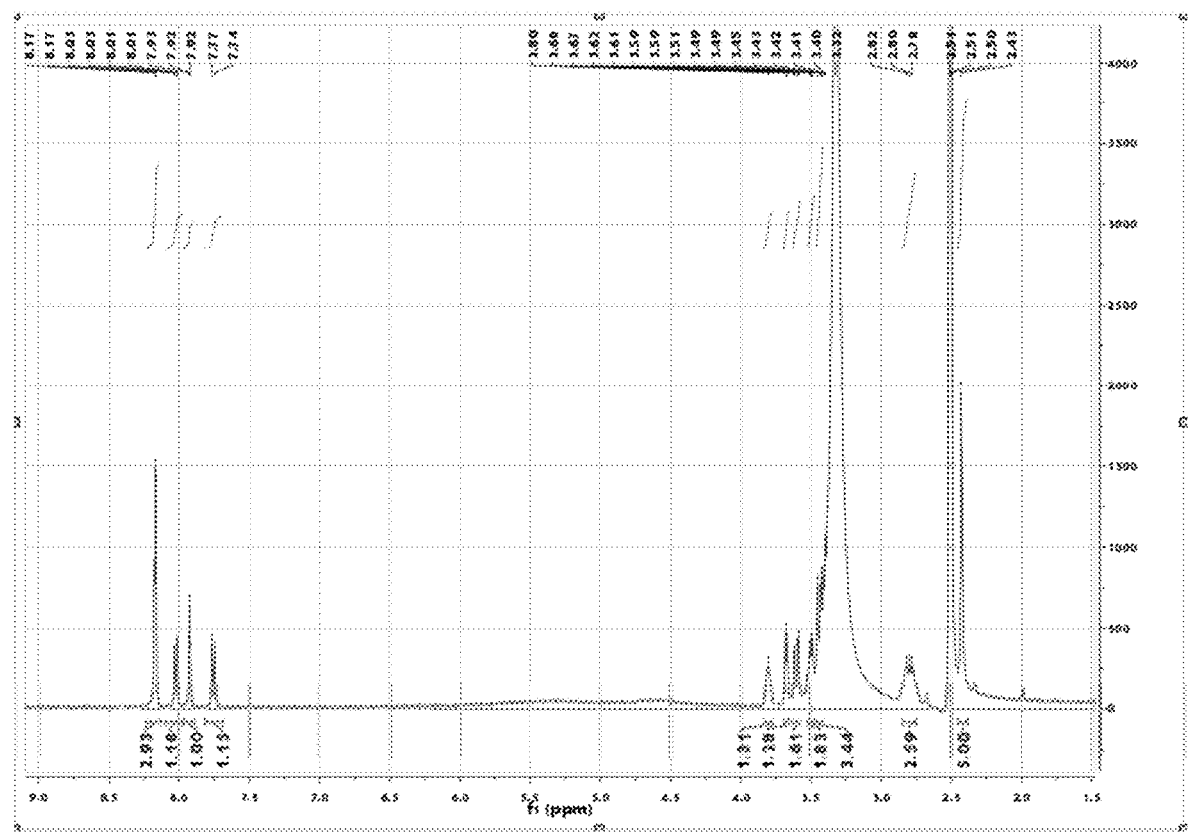
FIG. 5 shows a $^1$H Nuclear Magnetic Resonance spectrum of Form E in example 1.

The thermal gravimetric analysis (TGA) curve of Form E was substantially as depicted in FIG. 4. It has approximate 2.6% weight loss when heated to 120° C. The $^1$HNMR spectrum was substantially as depicted in FIG. 5.

TABLE 1

| 2θ | d spacing | Intensity % |
|---|---|---|
| 5.07 | 17.42 | 1.08 |
| 8.90 | 9.94 | 100.00 |
| 9.83 | 9.00 | 9.11 |
| 11.69 | 7.57 | 9.89 |
| 12.37 | 7.16 | 2.50 |
| 13.64 | 6.49 | 3.71 |
| 15.44 | 5.74 | 25.40 |
| 15.86 | 5.59 | 10.85 |
| 16.51 | 5.37 | 2.11 |
| 17.67 | 5.02 | 62.67 |
| 17.91 | 4.95 | 41.87 |
| 19.49 | 4.56 | 55.11 |
| 21.03 | 4.22 | 11.78 |
| 21.93 | 4.05 | 5.89 |
| 22.50 | 3.95 | 50.62 |
| 22.85 | 3.89 | 20.40 |
| 23.76 | 3.75 | 50.37 |
| 24.67 | 3.61 | 18.16 |
| 25.51 | 3.49 | 12.16 |
| 26.99 | 3.30 | 6.08 |
| 28.17 | 3.17 | 25.83 |
| 29.43 | 3.04 | 7.78 |
| 30.15 | 2.96 | 2.45 |
| 31.67 | 2.83 | 11.20 |
| 32.28 | 2.77 | 3.11 |
| 33.55 | 2.67 | 0.93 |
| 34.22 | 2.62 | 2.66 |
| 35.77 | 2.51 | 9.62 |
| 36.37 | 2.47 | 6.58 |
| 37.24 | 2.41 | 3.43 |
| 38.51 | 2.34 | 0.81 |
| 39.16 | 2.30 | 4.26 |

EXAMPLE 2

50.6 mg of Tafamidis free acid and 32.6 mg of meglumine were mixed evenly, and 2.5 mL of methyl isobutyl ketone (MIBK) was added. The mixture was stirred at room temperature for 96 hours to crystallize. White crystalline solid of Tafamidis meglumine was obtained by centrifugation and vacuum drying at room temperature.

Figure 2:
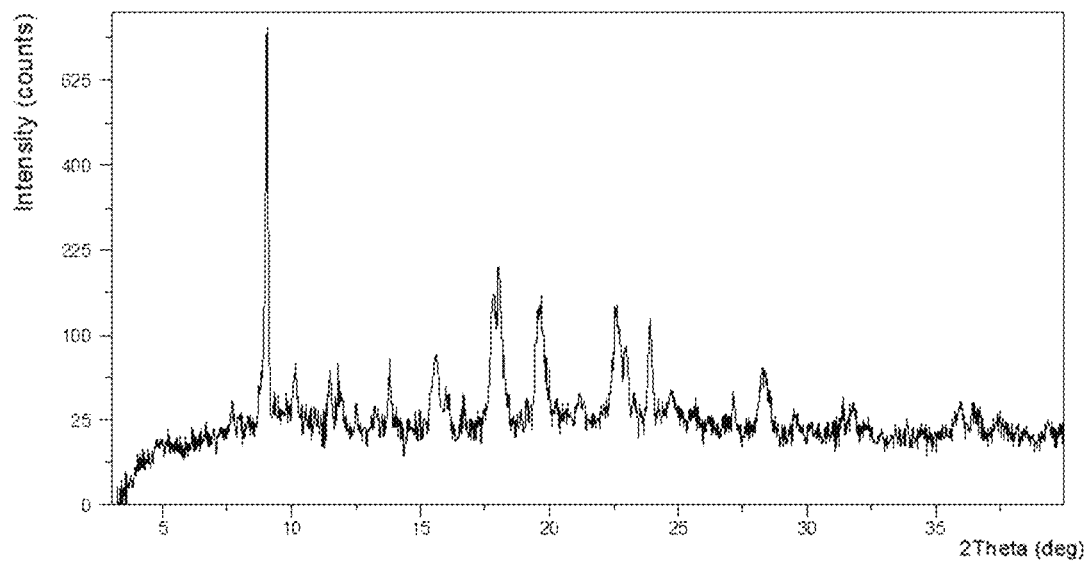
FIG. 2 shows an X-ray Powder Diffraction pattern of Form E in example 2.

The obtained solid conformed to Form E of the present disclosure, Its XRPD pattern was substantially as depicted in FIG. 2, and the XRPD data were listed in Table 2.

TABLE 2

| 2θ | d spacing | Intensity % |
|---|---|---|
| 8.90 | 9.94 | 100.00 |
| 9.97 | 8.87 | 5.66 |
| 11.33 | 7.81 | 4.45 |
| 13.65 | 6.49 | 5.93 |
| 15.45 | 5.74 | 7.70 |
| 17.62 | 5.03 | 13.80 |
| 17.89 | 4.96 | 22.95 |
| 19.39 | 4.58 | 11.43 |
| 22.45 | 3.96 | 13.71 |
| 22.85 | 3.89 | 6.63 |
| 23.74 | 3.75 | 10.52 |
| 27.02 | 3.30 | 2.28 |
| 28.15 | 3.17 | 5.60 |
| 31.48 | 2.84 | 1.39 |
| 35.96 | 2.50 | 1.31 |

EXAMPLE 3

51.7 mg of Tafamidis free acid and 31.7 mg of meglumine were mixed evenly, and were added into 2.5 mL of methyl tert-butyl ether (MTBE). The mixture was stirred at room temperature for 24 hours to crystallize. White crystalline solid of Tafamidis meglumine was obtained by centrifugation and vacuum drying at room temperature.

Figure 6:
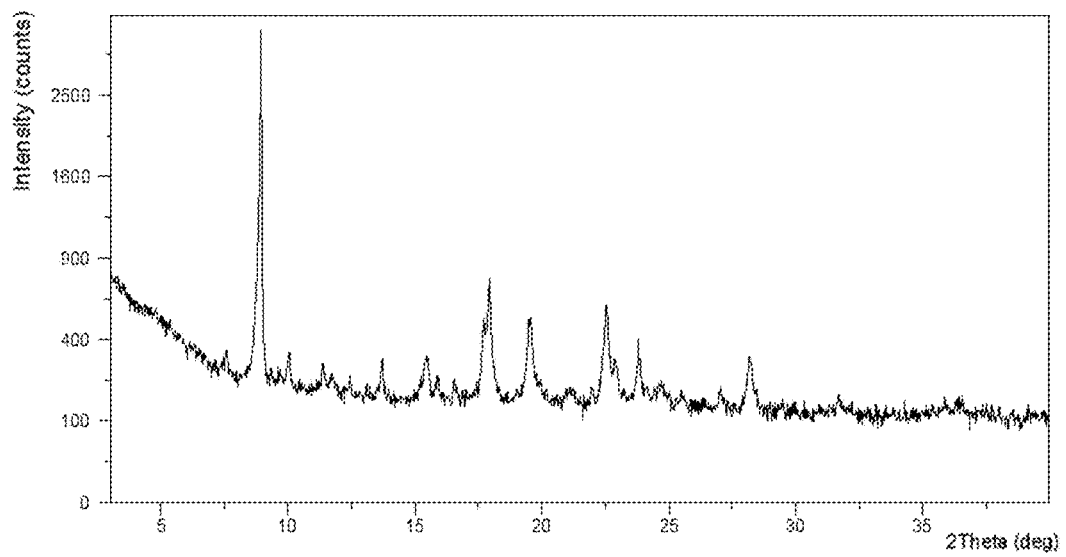
FIG. 6 shows an X-ray Powder Diffraction pattern of Form E in example 3.

The obtained solid conformed to Form E of the present disclosure, of which the XRPD pattern was substantially as depicted in FIG. 6, and the XRPD data were listed in Table 3.

TABLE 3

| 2θ | d spacing | Intensity % |
|---|---|---|
| 7.54 | 11.73 | 1.85 |
| 8.91 | 9.93 | 100 |
| 9.99 | 8.85 | 3.61 |
| 11.35 | 7.79 | 2.9 |
| 13.66 | 6.48 | 4.85 |
| 15.49 | 5.72 | 4.79 |
| 17.67 | 5.02 | 10.6 |
| 17.91 | 4.95 | 19.55 |
| 19.51 | 4.55 | 11.09 |
| 21.09 | 4.21 | 0.94 |
| 22.52 | 3.95 | 13.86 |
| 22.87 | 3.89 | 4.59 |
| 23.76 | 3.74 | 7.71 |
| 27.03 | 3.3 | 1.6 |
| 28.16 | 3.17 | 5.94 |
| 36.41 | 2.47 | 1.25 |

EXAMPLE 4

Figure 7:
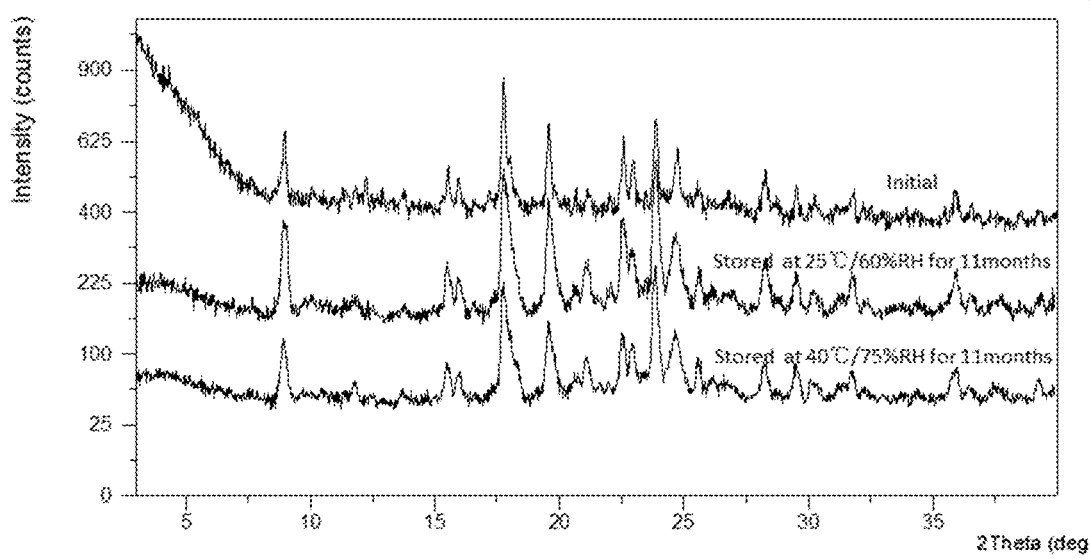
FIG. 7 shows X-ray Powder Diffraction patterns of Form E before and after storage at 25° C./60% RH and 40° C./75% RH for 11 months. The top, middle and bottom patterns corresponding to initial Form E, Form E after storage at 25° C./60% RH for 11 months and Form E after storage at 40° C./75% RH for 11 months, respectively.

Stability of Tafamidis Meglumine Form E:

Solid samples of Form E were stored under conditions of 25° C./60% relative humidity (RH) and 40° C./75% RH for 11 months and XRPD were tested. The XRPD patterns before and after storage were substantially as depicted in FIG. 7. The results are shown in table 4.

TABLE 4

| Initial Solid Form | Condition | Time | Final Solid Form |
|---|---|---|---|
| Form E | 25° C./60% RH | 11 months | Form E |
| Form E | 40° C./75% RH | 11 months | Form E |

Form E remains stable for at least 11 months under conditions of 25° C./60% RH and 40° C./75% RH. The above result shows that Form E has good stability. The XRPD patterns overlay are substantially as depicted in FIG. 7, in which the top, middle and bottom patterns correspond to the initial sample, sample stored at 25° C./60% RH for 11 months and sample stored at 40° C./75% RH for 11 months, respectively.

EXAMPLE 5

Figure 8:
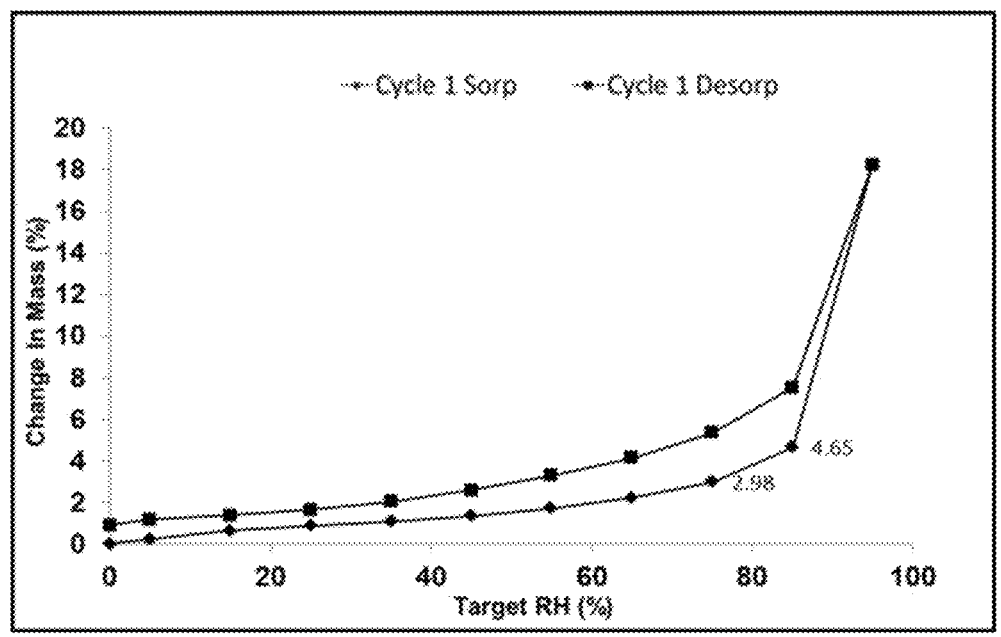
FIG. 8 shows Dynamic Vapor Sorption curve of crystalline form M in patent CN103781770B.
Figure 9:
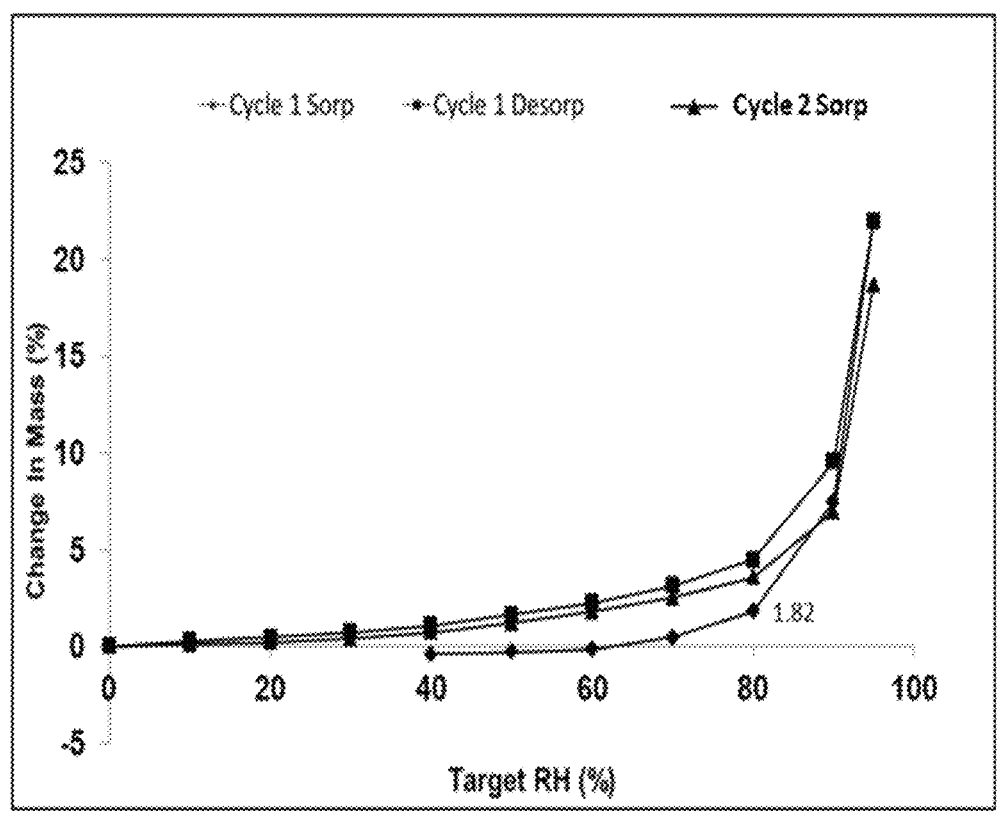
FIG. 9 shows Dynamic Vapor Sorption curve of Form E.

Hygroscopicity of Form M and Form E of Tafamidis Meglumine:

Dynamic vapor sorption (DVS) was applied to assess hygroscopicity of Form E and Form M in patent CN103781770B with about 10 mg of samples. The results were listed in Table 5. The DVS plots of Form E and Form M were substantially as depicted in FIG. 8 and FIG. 9, respectively.

TABLE 5

| Relative Humidity | Weight gain under 80% Relative Humidity |
|---|---|
| Form M | 2.98%-4.65% |
| Form E | 1.82% |

About hygroscopicity characterization description and definition of hygroscopicity (Chinese Pharmacopoeia 2015 edition general notices 9103 Drug hygroscopicity test guidelines, test at 25° C.+/−1° C., 80% Relative Humidity).

deliquescent: Sufficient water is absorbed to form a liquid;
very hygroscopic: Increase in mass is equal to or greater than 15 percent;
hygroscopic: Increase in mass is less than 15 percent and equal to or greater than 2 percent;
slightly hygroscopic: Increase in mass is less than 2 percent and equal to or greater than 0.2 percent.
no or almost no hygroscopic: Increase in mass is less than 0.2%.

Weight gain of Form E under 80% RH is 1.82%, belonging to slightly hygroscopic according to the guidelines described above. Weight gain of Form M under 75% RH is 2.98%. It can be clearly seen from FIG. 8 that weight gain of Form M under 80% RH will inevitably be larger than 2.98%, belonging to hygroscopic. The hygroscopicity of Form E is superior to that of Form M, which is beneficial to drug storage.

EXAMPLE 6

Purification Effect of Form E of Tafamidis Meglumine:

High Performance Liquid Chromatography (HPLC) was applied to test the chemical purities of Tafamidis free acid and Form E of Tafamidis meglumine. The results were listed in table 6 and table 7.

TABLE 6

HPLC results of Tafamidis free acid

| Peak number | Retention time (min) | RRT | Area (%) |
|---|---|---|---|
| 1 | 14.66 | 0.81 | 0.14 |
| 2 | 18.11 | 1.00 | 99.66 |
| 3 | 21.59 | 1.19 | 0.05 |
| 4 | 22.64 | 1.25 | 0.05 |
| 5 | 25.03 | 1.38 | 0.10 |

TABLE 7

HPLC results of Tafamidis meglumine

| Peak number | Retention time (min) | RRT | Area (%) |
|---|---|---|---|
| 1 | 14.91 | 0.82 | 0.12 |
| 2 | 18.30 | 1.00 | 99.88 |

The results show that the purity of Tafamidis meglumine Form E is 99.88%, which is higher than that of Tafamidis free acid (99.66%). It means that the purity is increased by the process described in above examples. It is well known that impurity control is a very important part in the production process of API. Apart from the advantages shown in the above examples, the novel crystalline form of the present disclosure also has purification effect.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A crystalline form E of Tafamidis meglumine shown as the following structure, wherein the X-ray powder diffraction pattern shows characteristic peaks at 2theta values of 8.9°±0.2°, 17.7°±0.2° and 19.5°±0.2° using CuKα radiation.

2. The crystalline form E of Tafamidis meglumine according to claim 1, wherein the X-ray powder diffraction pattern further shows 1 or 2 or 3 characteristic peaks at 2theta values of 22.5°±0.2°, 23.8°±0.2° and 28.2°±0.2°.

3. The crystalline form E of Tafamidis meglumine according to claim 1, wherein the X-ray powder diffraction pattern further shows 1 or 2 characteristic peaks at 2theta values of 15.4°±0.2° and 22.9°±0.2°.

4. A process for preparing crystalline form E of Tafamidis meglumine according to claim 1, wherein the process comprises: adding ketones, ethers or esters into a mixture of Tafamidis free acid and meglumine, stirring to crystallize at room temperature, and then separating and drying to obtain the Form E.

5. The process for preparing crystalline form E of Tafamidis meglumine according to claim 4, wherein, said ketones include methyl isobutyl ketone; said ethers include methyl tert-butyl ether; said esters include ethyl acetate.

6. A pharmaceutical composition, wherein said pharmaceutical composition comprises a therapeutically effective amount of crystalline form E of Tafamidis meglumine according to claim 1, and at least one pharmaceutically acceptable carrier, diluent or excipient.

7. A method for treating transthyretin familial amyloid polyneuropathy, comprising administering to a patient in need thereof a therapeutically effective amount of crystalline Form E of Tafamidis meglumine according to claim 1.

8. The crystalline form E of Tafamidis meglumine according to claim 1, wherein the X-ray powder diffraction pattern shows characteristic peaks at 2theta values of 8.9°±0.2°, 17.7°±0.2°, 19.5°±0.2°, 22.5°±0.2°, 23.8°±0.2° and 28.2°±0.2° using CuKα radiation.

9. The crystalline form E of Tafamidis meglumine according to claim 1, wherein the X-ray powder diffraction pattern shows characteristic peaks at 2theta values of 8.9°±0.2°, 17.7°±0.2°, 19.5°±0.2°, 22.5°±0.2°, 23.8°±0.2°, 28.2°±0.2°, 15.4°±0.2° and 22.9°±0.2° using CuKα radiation.

* * * * *